United States Patent

Hvass et al.

[11] Patent Number: 6,157,456
[45] Date of Patent: Dec. 5, 2000

[54] CUVETTE FOR SPECTROPHOTOMETRICAL ANALYSIS

[76] Inventors: Per Hvass, Önnemovägen 47, S-146 53 Tullinge; Teppo Tammi, Ribersborgavägen 13 B, S-217 54, Malmö, both of Sweden

[21] Appl. No.: 09/380,877

[22] PCT Filed: Mar. 11, 1998

[86] PCT No.: PCT/SE98/00443

§ 371 Date: Nov. 18, 1999

§ 102(e) Date: Nov. 18, 1999

[87] PCT Pub. No.: WO98/40720

PCT Pub. Date: Sep. 17, 1998

[30] Foreign Application Priority Data

Mar. 11, 1997 [SE] Sweden .................................. 9700875

[51] Int. Cl.[7] .............................. G01N 21/00; G01N 1/10
[52] U.S. Cl. ..................... 356/440; 356/244; 356/246; 422/102; 422/939; 435/288.4
[58] Field of Search ..................... 356/244, 246, 356/440, 318, 319, 326, 432, 434, 436; 436/164; 422/102, 104, 99, 939; 250/339.12, 339.06, 458.1, 576; 435/288.4, 305.2, 809

[56] References Cited

U.S. PATENT DOCUMENTS

| | | | |
|---|---|---|---|
| 3,936,196 | 2/1976 | Wickersheim | 356/246 |
| 4,605,305 | 8/1986 | Lenoir et al. | 356/246 |
| 4,682,891 | 7/1987 | De Macario et al. | 356/244 |
| 5,216,488 | 6/1993 | Tuunanen et al. | 356/440 |
| 5,290,705 | 3/1994 | Davis | 436/164 |
| 5,307,144 | 4/1994 | Hiroshi et al. | 356/244 |
| 5,453,252 | 9/1995 | Truett | 356/244 |
| 5,519,218 | 5/1996 | Chang | 356/244 |
| 5,723,341 | 3/1998 | Truett | 356/244 |
| 5,764,355 | 6/1998 | Gagnon et al. | 422/102 |

FOREIGN PATENT DOCUMENTS

| | | |
|---|---|---|
| 150804 | 6/1987 | Denmark . |
| 0135303 | 3/1985 | European Pat. Off. . |
| 0732578 | 9/1996 | European Pat. Off. . |
| 62-229046 | 10/1987 | Japan . |

*Primary Examiner*—Hoa Q. Pham
*Attorney, Agent, or Firm*—Young & Thompson

[57] ABSTRACT

The present invention relates to a cuvette (4) used for spectrophotometrical analyses, in which electromagnetic energy is passed through a liquid sample (8) contained therein. The object of the invention is to make the passage of the electromagnetic energy through the cuvette (4) and the liquid sample (8) independent of the material of the cuvette (4). This is done by providing the cuvette (4) with openings (14, 16; 22, 24) aligned to permit the electromagnetic energy to pass therethrough. The opening (14; 22, 24) in the or each side (12; 18, 20) making contact with the liquid sample (8) contained in the cuvette (4) is adapted to keep the liquid sample (8) within the cuvette (4) by means of its surface tension.

9 Claims, 1 Drawing Sheet

CUVETTE FOR SPECTROPHOTOMETRICAL ANALYSIS

BACKGROUND OF THE INVENTION

1. Field of the Invention

The present invention relates to a cuvette used for spectrophotometrical analyses, in which electromagnetic energy is passed through a liquid sample contained therein, such as a pure liquid, a solution, a dispersion, a colloidal solution or the like.

2. Description of the Prior Art

In such a cuvette the radiation beam generally enters the cuvette through one transparent end of the cuvette and exits the cuvette at the opposite end thereof, which end normally is an open end in direct contact with the surrounding environment. The characteristics of the beam emerging from the cuvette are then analysed to determine the composition of the fluid through which the radiation beam has passed and which is contained in the cuvette. Since the radiation beam has to pass through the cuvette, the transparent material thereof may cause artefacts such as scattering of the radiation beam, i.e. the determination of the composition of the fluid is dependable on the material of the cuvette.

EP 0 732 578 discloses a sample holder used for spectroscopy and is provided with a net, on which a sample liquid is applied. The fluid is applied in such a way that the liquid is spread over the mesh of the net. A radiation beam is passed through the liquid perpendicular thereto and the transmitted radiation is detected. The object of this disclosed sample holder is to properly dose the liquid to be radiated. This is done by securing that always the same amount of liquid will be absorbed in each mesh. The amount liquid present in the mesh of the net is then derived from a net constant. Even if the detected radiation through the liquid is independent of the material of the holder, the mesh can only hold a very small amount of liquid, i.e. only a film of liquid, and has not the capability to hold any larger quantities of liquid. JP-62-229046 discloses a particle detector comprising a fluid container provided with a porous film at the bottom end thereof. The porous film is designed to permit air/gas to pass there through, but prevent the fluid contained in the container to pass there through. It is the surface tension of the liquid that allows it to be kept in the container. The fluid container in this JP patent is presumably designed to be able to press gas through the bottom of the container without any leaking of fluid from the container.

U.S. Pat. No. 3,936,196 discloses a fluid chamber having manipulatable window elements. The chamber is provided with two transparent plates in order to permit light to enter and leave the chamber. This application recognises the problem that the material that the light has to pass on its way in and out of the chamber may impair the results obtained, when analysing the radiation passed through the chamber. This is especially true when the chambers contain gaseous materials, in which case a clouding or fogging of the transparent plate occurs. The fogged plate has then to be removed and cleaned before a new analyse can be performed. The fluid chamber according to the invention in this U.S. patent solves this problem by improving the structure of the transparent plate and thereby reduce the required frequency of cleaning or replacement of the plate to maintain a light transmittive area free of fogging.

Even if there have been made some attempts in prior art to increase the accuracy of spectrophotometrical analyses done on liquids, such as pure liquids, solutions, dispersions, colloidal solutions or the like, contained in a cuvette, there still is a need to make the spectrophotometrical analyses truly independent of the cuvette material.

SUMMARY OF THE INVENTION

Thus, the object of the present invention is to eliminate the affects of the cuvette material on the spectrophotometrical analyses performed on a liquid contained in the cuvette.

This object is solved by a cuvette for spectrophotometrical analyses, in which electromagnetic energy is passed through a liquid sample contained therein, said cuvette comprising a first side through which the electromagnetic energy enters and a second opposite side through which the electromagnetic energy leaves, and wherein the first side and the second side each are provided with an opening, said openings being aligned to permit the electromagnetic energy to pass there through.

In a preferred embodiment of the invention the area of the opening in the or each side making contact with the liquid sample contained in the cuvette is adapted to keep the liquid sample within the cuvette by means of its surface tension. Preferably such an adapted opening is provided with a circumferential ridge.

According to the invention the alignment of the openings may be chosen freely such as in a horizontal plane of the cuvette, in a vertical plane of the cuvette or in any other suitable direction, i.e. the cuvette in the present invention may be adapted to any suitable radiation and detection system.

Furthermore, the relation between the diameter for the opening in the or each side making contact with the liquid sample contained in the cuvette and the thickness of that side is preferably 2:5 in order to safely keep the liquid sample inside the cuvette by means of its surface tension.

the present invention is also directed towards a microtitre plate comprising a plurality of cuvettes as described above.

The arrangement of two aligned openings according to the present invention allows the electromagnetic energy to pass through only the liquid sample, without having to pass through the material of the cuvette. Thus, the solution of the present invention makes spectrophotometrical analyses that use such a cuvette truly independent of the material of the cuvette.

Furthermore, the openings provided in the cuvette of the present invention are adapted to keep the liquid sample within the cuvette by means of its surface tension, i.e. there will be no leakage from the cuvette even though it is provided with openings in contact with the sample liquid.

BRIEF DESCRIPTION OF THE DRAWINGS

The foregoing and other aspects of the present invention will be best appreciated with reference to the following detailed description of specific embodiments of the invention, given by way of example only, when read in conjunction with the accompanying drawings, wherein.

DESCRIPTION OF THE PREFERRED EMBODIMENTS

Figure 1:
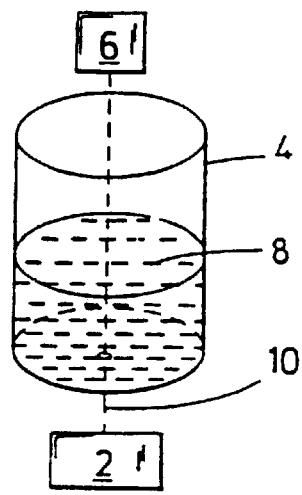
FIG. 1 is a schematic view of a spectrophotometrical system.

FIG. 1 shows a schematic view of a spectrophotometrical system, comprising a radiation source 2, a cuvette 4 and a detection device 6. As can be seen in FIG. 1 the cuvette 4 contains a liquid sample 8 of which some properties are to be determined by spectrophotometrical analyses. The liquid sample 8 may be any liquid such as a pure liquid, a solution, a dispersion, a colloidal solution or the like.

The cuvette 4 generally comprises a transparent tube of glass or plastic having a circular or square shaped cross section, but any other shape or material may be used without departing from the scope of the invention. To avoid any influences that the material of the cuvette 4 may have on the result obtained, when analysing the radiation passed there through, the cuvette 4 is provided with two openings, to be described in detail below.

The radiation source 2 in such a spectrophotometrical system is generally arranged to radiate a beam 10 directed to enter the cuvette 4, pass trough the liquid sample 8 provided therein and impinge on the detection device 6. The radiation source 2 may be a laser, an infrared light source or any other suitable means that sends out electromagnetic energy. The detection device 6 may be a photo transistor, a photo multiplier or the like, depending on the resolution needed to determine the desired properties. It is believed to be within the skills of a person in the art to arrange and set up such a radiation and detection system and is therefore not described in detail herein.

The cuvette 4 which is the subject of the present invention will now be described by way of preferred embodiments, shown in FIGS. 2 and 3. In these figures the radiation beam 10 and the liquid sample 8 will be included to clearly show the path for the electromagnetic energy through the cuvette openings and the liquid sample 8 contained therein.

Figure 2:
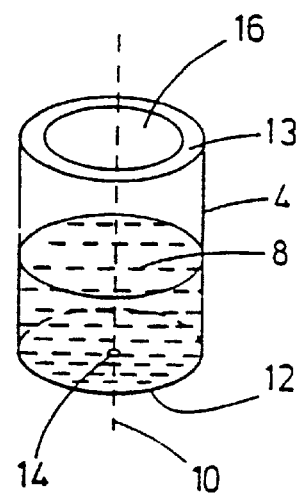
FIG. 2 is a first embodiment of the cuvette according to the invention.

In a first embodiment of the invention, shown in FIG. 2, the cuvette 4 has a circular cross section having a bottom wall or side 12 and a top wall or side 13. The bottom wall 12 and the top wall 13 are opposite each other. The bottom wall 12 of the cuvette 4 is provided with a small circular opening 14 and the top wall 13 of the cuvette 4 with a sample filling opening 16. In this first embodiment the electromagnetic energy, i.e. beam 10, will enter the cuvette 4 through the small opening 14, pass the liquid sample 8 and finally leave the cuvette 4 through the sample filling opening 16. The two openings 14, 16 are with other words aligned in a vertical plane of the cuvette 4.

In this particular embodiment of the invention the liquid sample 8 is in direct contact with the bottom wall 12 of the cuvette 4 and thereby with the small opening 14. The size of the small opening 14 is therefore adapted to keep the liquid sample 8 within the cuvette 4 by means of its surface tension. The sample filling opening 16 provided on the top wall 13 is not in contact with the liquid sample 8 and its size may therefore be determined without such considerations and may take up the entire surface of the top wall 13, i.e. the sample filling opening 16 may constitute a virtual top wall.

Figure 3:
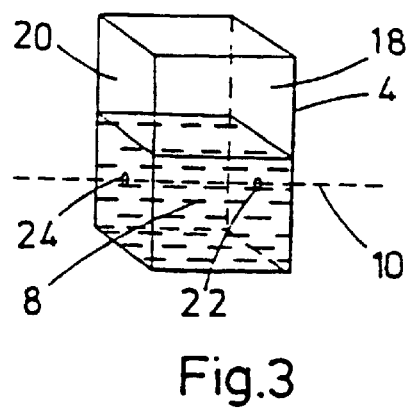
FIG. 3 is a second embodiment of the cuvette according to the invention.

In a second embodiment of the invention, shown in FIG. 3, the cuvette 4 has a square shaped cross section having a first side 18 and a second side 20. The firs side 18 and the second side 20 are opposite each other. Both the first side 18 and the second side 20 is provided with a small opening 22 and 24, respectively. The two openings 22, 24 are with other words aligned in a horizontal plane of the cuvette 4, as can be seen by the beam 10 passing through these openings 22, 24 and the sample liquid 8.

In this second embodiment of the cuvette 4 the liquid sample 8 is in contact with both the openings 22, 24, and their size is therefore adapted to keep the liquid sample 8 within the cuvette 4 by means of its surface tension.

As can be noted in the two embodiments described above, the size of the openings in contact with the liquid sample 8 have to be designed correctly in order to keep the liquid sample 8 within the cuvette 4. The size of the small openings is not only dependent on the type of liquid used as a sample 8, but also on the thickness of the wall or side of the cuvette 4 on which they are provided. A thicker wall will allow a larger diameter for the small opening, due to capillary forces. If for example the liquid sample 8 has properties close to or such as bodily fluids a suitable relationship between the diameter of the small opening and the thickness of the wall would be approximately 2:5. Given that the thickness of the wall is 0.5 mm the diameter of the small opening would be 0.2 mm.

Figure 4:
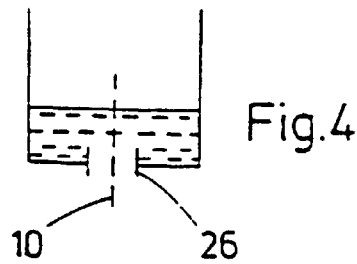
FIG. 4 is a close up view showing one opening of the cuvette in detail.

In a particular embodiment of the small opening in the cuvette 4, shown in FIG. 4, the small opening 14 is provided with a circumferential ridge 26. This ridge 26 may be used as an alternative to making the wall of the cuvette 4 thicker. By using such a ridge 26 the wall may be made thinner without having the drawback of decreasing the capillary forces keeping the liquid sample 8 inside the cuvette 4. It shall be noted that the figures illustrating the invention not are drawn in scale, and are only intended to illustrate the principles of the invention.

As can be noted by the two described embodiments of the cuvette 4, i.e. the one with vertical aligned openings 14, 16, and the one with horizontal aligned openings 22, 24, the actual position of the openings is not critical in order to carry out the invention. The important thing being that the cuvette 4 is provided with two openings aligned to permit the electromagnetic energy from the radiation source 2 to pass there through and also trough the liquid sample 8 contained in the cuvette 4. The openings do further not need to be a combination of one small opening 14 and one large sample filling opening 16 for the horizontal embodiment and two small openings 22, 24 for the vertical embodiment, the important thing being that the opening in the or each side making contact with the liquid sample 8 contained in the cuvette 4 is provided with an opening having a small diameter in order to keep the liquid sample within the cuvette by means of its surface tension.

The use of two openings with a small diameter would not only be the case when the openings are aligned in a horizontal plane of the cuvette 4, as in the second embodiment, but would also be the case if the openings were aligned in a vertical plane of the cuvette 4 provided that the cuvette 4 was completely filled with liquid sample 8.

It shall also be understood that the invention is not limited to arranging the openings in a vertical or horizontal plane. The direction of alignment may be chosen freely. Thus, the cuvette 4 according to the present invention may readily be adapted to the radiation and detection system used in order to perform the spectrophotometrical analyses.

Furthermore it shall be noted that even if the small opening 14 described above has a circular shape, the invention may be practised with a small opening having other shapes, such as triangular or rectangular shapes, etc.

Figure 5:
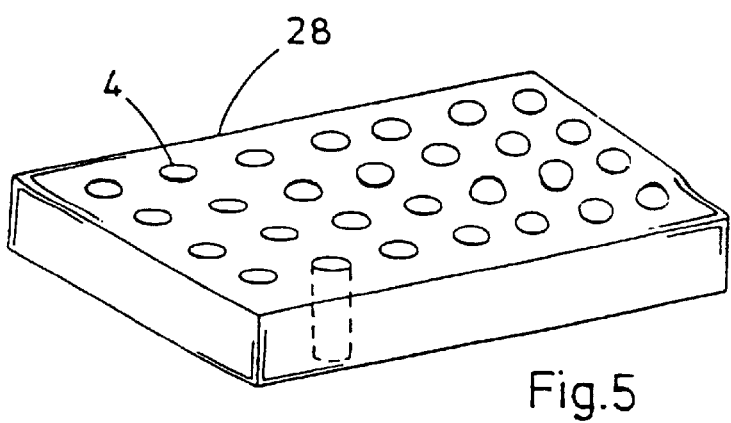
FIG. 5 shows a microtitre plate comprising a plurality of cuvettes according to the invention.

A further embodiment of the invention is shown in FIG. 5 and is a microtitre plate 28 comprising a plurality of individual cuvettes 4.

Although specific embodiments of the invention have been set forth herein in some detail, it is to be understood that this has been done for purposes of illustration only, and is not to be taken as a limitation on the scope of the invention as defined in the appended claims.

What is claimed is:

1. Cuvette used for spectrophotometrical analyses, in which electromagnetic energy is passed through a liquid sample (8) contained therein, comprising a first side (12; 18) through which the electromagnetic energy enters and a second opposite side (13; 20) through which the electromagnetic energy leaves, characterised in that the first side (12; 18) and the second side (13; 20) each are provided with an opening (14, 16; 22, 24), said openings (14, 16; 22, 24) being aligned to permit the electromagnetic energy to pass there through.

2. Cuvette according claim 1, characterised in that the area of the opening (14; 22, 24) in the or each side (12; 18, 20) making contact with the liquid sample (8) contained in the cuvette (4) is adapted to keep the liquid sample (8) within the cuvette (4) by means of its surface tension.

3. Cuvette according to claim 1, characterised in that the opening (14; 22, 24) in the or each side (12; 18, 20) making contact with the liquid sample (8) contained in the cuvette (4) is provided with a circumferential ridge (26).

4. Cuvette according to claim 1, characterised in that the openings (14, 16) are aligned in a vertical plane of the cuvette (4) and have a circular cross section.

5. Cuvette according to claim 4, characterised in that the relation between the diameter of the opening (14; 22, 24) in the or each side (12; 18, 20) making contact with the liquid sample (8) contained in the cuvette (4) and the thickness of that side (12; 18, 20) is 2:5.

6. Cuvette according to claim 4, characterised in that the diameter of the opening (14; 22, 24) in the or each side (12; 18, 20) making contact with the liquid sample (8) contained in the cuvette (4) is 0.2 mm.

7. Cuvette according to claim 1, characterised in that the openings (22, 24) are aligned in a horizontal plane of the cuvette (4) and have a circular cross section.

8. Cuvette according to claim 1, characterised in that the first side is the bottom wall (12) of the cuvette (4) and is in contact with the liquid sample (8) contained in the cuvette (4) and that the second side (13) constitutes a sample filling opening (16).

9. Microtitre plate (28), comprising a plurality of cuvettes (4), each cuvette comprising a first side (12; 18) through which electromagnetic energy enters and a second opposite side (13; 20) through which electromagnetic energy leaves, characterised in that the first side (12; 18) and the second side (13; 20) each are provided with an opening (14, 16; 22, 24), said openings (14, 16; 22, 24) being aligned to permit the electromagnetic energy to pass therethrough.

* * * * *